United States Patent [19]
Yeh et al.

[11] Patent Number: 5,302,713
[45] Date of Patent: Apr. 12, 1994

[54] METHOD FOR THE PREPARATION OF DELTA3-7-SUBSTITUTED AMINO DESACETOXY CEPHALOSPORANIC ACID

[75] Inventors: Jinun B. Yeh; Lain-Tze Lee; Mei-Hueih Chen, all of Hsinchu, Taiwan

[73] Assignee: Industrial Technology Research Institute, Hsinchu, China

[21] Appl. No.: 861,232

[22] Filed: Mar. 31, 1992

[51] Int. Cl.$^5$ .............................. C07D 501/10
[52] U.S. Cl. .................. 540/230; 540/221; 540/222; 540/228
[58] Field of Search ............ 540/222, 227, 221, 230, 540/228

[56] References Cited

U.S. PATENT DOCUMENTS

| | | | |
|---|---|---|---|
| 3,658,799 | 4/1972 | Eardley et al. | 260/243 C |
| 3,725,397 | 4/1973 | Graham et al. | 260/243 C |
| 3,944,545 | 3/1976 | Chou | 260/243 C |
| 4,003,894 | 1/1977 | Verweij et al. | 260/243 C |

Primary Examiner—Nicholas S. Rizzo
Attorney, Agent, or Firm—Darby & Darby

[57] ABSTRACT

A method for synthesizing $\Delta^3$-7-substituted amino desacetoxy cephalosporanic acid from a penicillin sulfoxide or its alkylsilylated ester derivative is provided. According to the method, penicillin sulfoxide is heated in the presence of an organic ammonium salt catalyst and a copolymer composed of dimethylsilane and urea units until formation of the cephalosporanic acid occurs by ring expansion reaction. The copolymer functions both as a dehydrating agent for removing the water by-product generated from the reaction as well as an esterifying agent for converting penicillin sulfoxide into its dimethylsilyl ester derivative. The method of the invention produces high yields of the cephalosporanic acid and avoids the need for excess dimethylsilyating agents.

15 Claims, No Drawings

METHOD FOR THE PREPARATION OF DELTA3-7-SUBSTITUTED AMINO DESACETOXY CEPHALOSPORANIC ACID

FIELD AND BACKGROUND OF THE INVENTION

Cephalosporins are a group of antibiotics derived from *Cephalosporium Acremonium*, a fungus first isolated from sand near the Sardinia sea shore by Brotju in 1948. Naturally occuring cephalosporins, such as cephalosporin P, N, and C, have been discovered in *C. Acremonium* culture medium and were found to have bacteriostatic activities against *Staphyllococcos aureus*.

Among the three natural cephalosporins, cephalosporin C closely resembles penicillin both in terms of having a fused beta-lactam ring and having a broad antibiotic activity, however its very weak clinical effect has limited its use as an antibiotic. Accordingly, much research has been devoted towards the synthesis of semisynthetic cephalosporin analogs with the goal of creating useful semi-synthetic, broad spectrum antibiotics having bacteriocidal or bacteriostatic activity against Gram positive and Gram negative bacteria.

A number of synthetic routes for preparing semisynthetic cephalosporin antibiotics, starting from 7-aminocephalosporanic acid (7-ACA), have been reported. For example, the D-2-amino adipic acid side chain of cephalosporin C can be hydrolyzed to yield 7-ACA as shown in the following equation

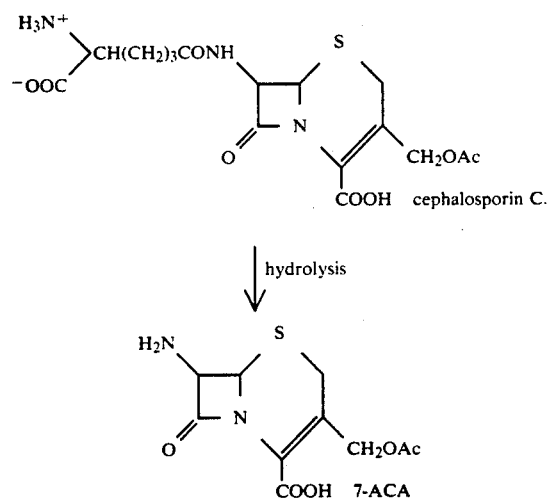

Many kinds of functional groups can be introduced into the 7-and 3-positions of 7-ACA, thereby a variety of semisynthetic cephalosporanic antibiotics can be produced by such chemical modification.

In addition, if the substituent on C3 of 7-ACA were modified to $CH_3$-group, many antibiotics suitable for oral administration could thus be synthesized. The acetoxy group on $CH_3$ of 7-ACA can be removed to form 7-aminodesacetoxy cephalosporanic acid (7-ADCA), an intermediate between cephem and penam. That is, 7-ADCA can be produced by reduction of 7-ACA derivatives or by oxidation of 6-APA derivatives.

In one method, 7-ADCA was prepared by reduction of 7-ACA as shown in the following equation:

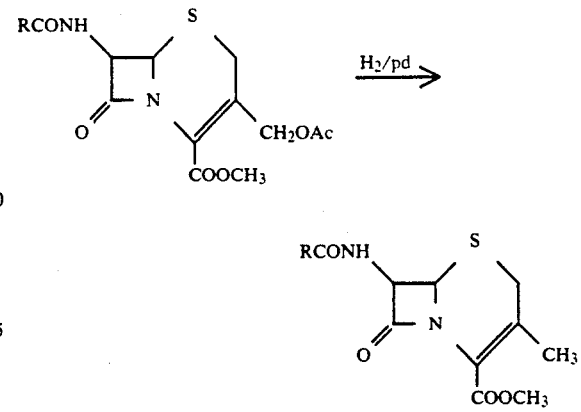

The product resulting from this reaction, however, is costly due to the use of expensive 7-ACA as starting material and nobel metal as catalyst.

Another method for the preparation of 7-ACDA is based on ring expansion of penicillin starting materials. Its synthetic route is as follows:

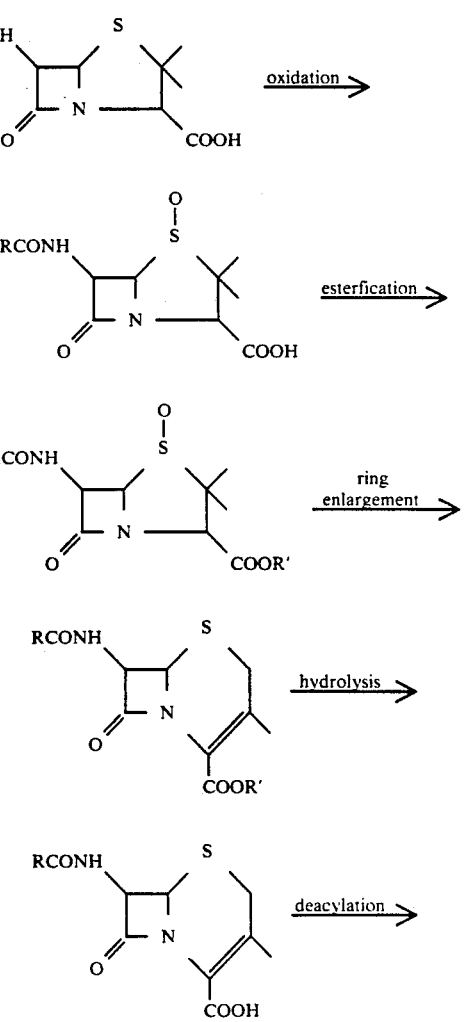

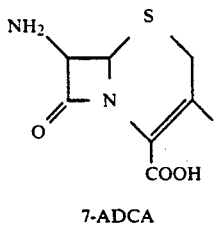

7-ADCA

Pencillin G (R=—CH$_2$—φ) or penicillin V (R=—CH$_2$—O—φ) can be oxidized in water with periodic acid or peracetic acid as oxidant to form its corresponding sulfoxide. The sulfoxide is esterified to protect its carboxylic group, then heated in the presence of an acid catalyst to carry out the ring enlargement reaction. The product is then hydrolyzed to remove the protecting group and deacetylated by chemical or enzymatic methods to produce 7-ADCA.

The aforementioned process comprises oxidation, esterification, ring enlargement, hydrolysis, and deacetylation. Among which, the reagent selected for the esterification can affect not only the facility and yields of the esterification and hydrolysis reactions, but also influences the selectivity of ring enlargement reaction. In commercialized processes, the protecting ester groups used include trichloroethyl (U.S. Pat. No. 3,725,397), dibenzylmethyl (U.S. Pat. No. 3,658,799), and trimethylsilyl (U.S. Pat. No. 3,944,545) groups.

When alkylsilylating agents are employed, both esterification and hydrolysis can be carried out easily and produce high yields of the product. Furthermore, when alkylsilylating agent is used as dehydrating agent in the ring enlargement reaction, under the strong interaction between alkylsilylating agent and water, esterification, ring enlargement reaction and hydrolysis can be readily accomplished in one pot.

For the ring enlargement reaction, the presence of chloride ion or minor changes in the acidity or basicity of the reaction mixture can significantly affect the yield of the product. Similarly, different kinds of alkylsilylating agents and compositions of alkylsilylated products can produce various effects as well.

To avoid the effect of acidity and basicity and of chloride ion on the labile alkylsilylated ester product, neutral alkylsilylating agents have been employed in the ring enlargement reaction. For example, U.S. Pat. No. 4,003,894) describes the use of N,O-bis (trimethyl silyl) acetamide, or N,N'-bis (trimethyl silyl) urea which produce relatively good results. These reagents, however, are very costly. Moreover, in order to prevent destruction of the alkylsilylated penicillin ester by water produced in the ring enlargement reaction, excess amounts of the alkylsilylating agent, in amounts of three to four times the mole equivalent of the penicillin ester, are required. Thus, the cost of the alkylsilylating agent dominates the production cost of 7-ADCA.

Accordingly, there is a need in the art for a commercially useful method of producing 7-ADCA in high yields and which avoids the use of excessive amounts of costly neutral alkylsilylating agents.

SUMMARY OF THE INVENTION

The invention provides a method for preparing Δ$^3$-7-substituted amino desacetoxy cephalosporanic acid by a modification of the ring enlargement reaction. According to the present method, Δ$^3$-7-substituted amino desacetoxy cephalosporanic acid is obtained by heating penicillin sulfoxide or its alkylsilyl ester derivative, in the presence of an organic ammonium salt as catalyst and a suitable solvent, with a copolymer composed of dimethylsilane and urea units. The copolymer serves as dehydrating agent which removes water, a by-product of the reaction, as well as an esterifying agent to form dimethylsilyl esters of the penicillin sulfoxide. The use of the copolymer in the ring expansion method reaction avoids the need for excess amounts of expensive neutral alkylsilylating agents.

Accordingly, it is an object of the invention to provide a method for the preparation of Δ$^3$-7-substituted amino desacetoxy cephalosporanic acid from penicillin sulfoxide using a modified ring expansion reaction which utilizes a copolymer composed of dimethylsilane and urea units.

This and other objects of the invention will be apparent in view of the detailed description below.

DETAILED DESCRIPTION OF THE INVENTION

According to the method of the present invention, neutral dimethylsilyating agent is first prepared by reacting dichlorodimethylsilane, with ammonia gas, in a suitable dried organic solvent.

Dichlorodimethylsilane is dissolved in a suitable organic solvent and reacted with excess ammonia gas, under an inert atmosphere, until ammonia uptake by the reaction mixture no longer occurs. The uptake of ammonia gas in the reaction generally occurs between about 30 and about 60 minutes.

The amount of dichlorodimethylsilane that is used in making the neutral dimethylsilylating agents is generally between about 0.5 and about 2 moles, preferably about 1.0 moles, per liter of solvent.

Suitable, but non-limiting, solvents for use in this reaction include toluene, dioxane, dimethyl formamide (DMF), pyridine, or trichloroethane. A particularly preferred solvent for preparing the neutral dimethylsilylating agents is trichloroethane.

The reaction is generally conducted at a temperature ranging between about 5° C. and about 40° C., preferably about 25° C.

The resulting solution contains a near quantitative yield of a mixture of neutral dimethylsilylating agents, hexamethylcyclotrisilazane and octamethylcyclotetrasilazane, as well as ammonium chloride as a precipitate. Thereafter, the ammonium chloride was filtered off, preferably under an inert atmosphere, leaving a filtrate containing the mixture of hexamethylcyclotrisilazane and octamethylcyclotetrasilazane.

The concentration of the cyclosilazanes (hexamethylcyclotrisilazane and octamethylcyclotetrasilazane) in the filtrate solution is generally between about 5 and about 20%, preferably about 10% (W/V).

Thereafter, a volume of the filtrate solution containing the cyclosilazanes, ammonium bromide as catalyst, urea, and a suitable solvent (described above), are added into a reaction flask. The reaction mixture, while stirring, is heated to a temperature between about 80° C. and about 150° C., preferably about 114° C., and maintained at this temperature until ammonia gas is no longer emitted from the reaction mixture. The reaction mixture, comprising a copolymer composed of dimethylsilane and urea units, has a viscous opaque appearence.

The mole ratio of urea to cyclosilazanes is generally between about 1:1 and about 2:1, preferably about 1:1.

The amount of ammonium bromide catalyst that is used in this reaction is generally between about 0.1 and about 3 grams per 100 ml of reaction solution.

Thereafter, the reaction mixture is heated at constant temperature for an additional period of at least 15 minutes to ensure completion of the polymerization reaction, then cooled to a temperature between about 50° C. and about 100° C., preferably about 80° C., prior to addition of the penicillin sulfoxide.

Thereafter, penicillin sulfoxide is added directly into the reaction flask containing the copolymer, along with an organic ammonium salt catalyst. The reaction was then heated to a temperature between about 80° C. and about 150° C., preferably about 114° C., for a period ranging between about 30 and about 60 minutes, preferably about 30 minutes, during which time the ring expansion reaction occurs.

The amount of organic ammonium salt catalyst that is employed in the ring expansion reaction is generally between about 1 and about 3 g, preferably about 2.2 g, per 100 ml of the reaction solution.

Suitable, but non-limiting, examples of organic ammonium salts as catalysts include mineral acid and organic acid salts of pyridine, aniline and N-alkylaniline, e.g. N-methylaniline. Representative examples include hydrobromic acid, hydrochloric acid, phosphoric acid, sulfuric acid, trichloroacetic acid, and p-toluenesulfonic acid salts of pyridine, aniline and N-alkylaniline. A preferred catalyst for use in the ring expansion reaction is pyridine hydrobromide.

After a period of about 30 minutes, additional organic ammonium salt catalyst was added into the reaction mixture in an amount of between about 0.5 and about 1.0 g, preferably about 0.6 g. Thereafter, the temperature of the reaction mixture was maintained for a final period of about 60 and 100 minutes, preferably about 80 minutes, to ensure maximum reaction.

Thereafter, water is added to the reaction mixture and the pH of the mixture was adjusted to about pH 8 with 1 N aqueous sodium hydroxide solution Active carbon (0.5 g) was added to the water layer to decolorize the solution The solution was then filtered to remove the carbon particles and the filtrate was acidified to about pH 1.5 with an aqueous acid solution, e.g. 1 N HCl, producing a suspension containing $\Delta^3$-7-substituted amino desacetoxy cephalosporanic acid (7-ADCA) which was collected by filtration.

In another embodiment of the method of the present invention, a separate alkylsilyating agent, e.g. 1,1,1,3,3,3-hexamethyldisilazane, or a slight excess of hexamethylcyclotrisilazane or octamethylcyclotetrasilazane, relative to urea, is added to the reaction flask prior to formation of the copolymer. The alkylsilylating agent reacts with the penicillin sulfoxide, generating the alkylsilyl ester, e.g. dimethylsilyl ester, of penicillin, prior to ring expansion.

The process of the present invention produces a good yield of 7-ADCA using between about one to about two mole equivalents of dimethylsilylating agent to that of penicillin sulfoxide, representing only 25% to 67% of the reported amount of dimethylsilylating agent that is generally used in the ring expansion reaction.

The following examples illustrate the present invention but do not serve to limit its scope.

EXAMPLE 1

To a 12-liter three-neck reactor equipped with a mechanical stirrer, a condenser and an ammonia gas inlet, 1,1,2-trichloroethane (5.4 liter) and dichlorodimethylsilane (600 ml, 5 mole), were added and stirred under jacketed water bath at room temperature. The reaction solution was then purged with ammonia gas (400 liter) and resulted in precipitation of ammonium chloride. Thereafter, the ammonium chloride was filtered off, leaving a filtrate containing a mixture of hexamethylcyolotrisilazane and octamethylcyclotetrasilazane in near quantitative yield.

EXAMPLE 2

To a 250-ml three-neck reactor equipped with mechanical stirrer, a condenser and a thermometer, under a nitrogen atmosphere, urea (2.6 g), trace ammonium bromide as catalyst, filtrate in Example 1 (50 ml) and 1,1,2-triohloroethane (50 ml) were added, stirred and heated to reflux at about 114° C., producing ammonia gas. After stirring for 15 minutes, the reaction mixture became viscous opaque. The mixture was heated for an additional one hour, and then cooled to 80° C. Pyridine-HBr (2.2 g) as catalyst and penicillin G sulfoxide (5.25 g, 0.015 mole) were added and the reaction solution stirred for 10 minutes and then heated reflux to about 114° C. After 30 minutes, additional pyridine-Hbr (0.6 g) was added and heating continued for an additional 80 minutes. After the reaction was completed, 83% yield of the product was produced as determined by HPLC. Water (80 ml) was added and pH was adjusted to 8 with 1 N aqueous sodium hydroxide solution. To the water layer, active carbon (0.5 g) was added to decolour the solution. The solution was filtered and pH of the filtrate was adjusted to 1.5 and was then filtered to yield the pale yellow solid $\Delta^3$-7-substituted amino desacetoxy cephalosporanic acid (3.98 g).

EXAMPLE 3

To a 250-ml three-neck reactor equipped with a mechanical stirrer, a condenser and a thermometer, under a nitrogen atmosphere, urea (2.6 g),, trace ammonium bromide as catalyst, filtrate in Example 1 (40 ml), 1,1,1,3,3,3-hexamethyldisilazane (2 ml), and 1,1,2-trichlorethane (60 ml) were added, the solution stirred then heated to reflux at about 114° C. Ammonia gas was generated during this process. After stirring for 15 minutes, the reaction mixture became viscous opaque. The mixture was continuously heated for one hour further, and then cooled to 80° C. Pyridine-HBr (2.2 g) as catalyst and penicillin G sulfoxide (5.25 g, 0.015 mole) were added to the mixture and stirred for 10 minutes and then heated reflux to about 114° C. After 30 minutes, additional pyridine-HBr (0.6 g) was added and the reaction mixture was heated for an additional 80 minutes. After the reaction was completed, 86% yield was obtained as determined by HPLC. Products were separated according to procedure described in Example 2.

EXAMPLE 4

The procedure described in Example 3 was repeated with different types of organic ammonium salts as catalysts for the ring enlargement reaction, as shown in the Table below, together with the yields:

| No. | Catalyst | Amount (g) | Additional amount after 30 min. (g) | Yield (%) |
|-----|----------|------------|-------------------------------------|-----------|
| 1.  | Pyridine-HCl | 1.6 | 0.4 | 55 |
| 2.  | Pyridine-H₃PO₄ | 2.4 | 0.7 | 68 |
| 3.  | Pyridine-1,1,1-trichloroethyl phosphate | 4.4 | 1.2 | 76 |
| 4.  | Pyridine sulfate | 2.4 | 0.7 | 49 |
| 5.  | Pyridine trichloroacetatic acid | 3.3 | 0.9 | 63 |
| 6.  | Pyridine p-toluenesulfonic acid | 3.5 | 1 | 43 |
| 7.  | 2-Methylpyridine hydrobromide | 2.4 | 0.7 | 84 |
| 8.  | Aniline hydrobromide | 2.4 | 0.7 | 75 |
| 9.  | N-methylaniline hydrobromide | 2.7 | 0.8 | 73 |
| 10. | Triethylamine hydrobromide | 2.5 | 0.7 | 53 |

EXAMPLE 5

The procedure described in Example 3 was repeated using different amounts of pyridine-HBr as the catalyst. The following results were obtained:

| No. | Amount of catalyst (g) | Additional amount after 30 min. (g) | yield (%) |
|-----|------------------------|-------------------------------------|-----------|
| 1.  | 4.0 | 0.6 | 69 |
| 2.  | 3.0 | 0.6 | 78 |
| 3.  | 2.6 | 0.6 | 84 |
| 4.  | 2.2 | 0.6 | 86 |
| 5.  | 2.0 | 0.6 | 80 |
| 6.  | 1.5 | 0.6 | 67 |
| 7.  | 2.8 | —   | 80 |

EXAMPLE 6

The procedure described in Example 3 was repeated with different volumes of filtrate solution prepared in Example 1. The following results were obtained:

| No. | Solution in Example 1 (ml) | Diluent* (ml) | Yield (%) |
|-----|----------------------------|---------------|-----------|
| 1.  | 80 | 20 | 84 |
| 2.  | 60 | 40 | 84 |
| 3.  | 50 | 50 | 85 |
| 4.  | 40 | 60 | 86 |
| 5.  | 30 | 70 | 83 |
| 6.  | 20 | 80 | 66 |

EXAMPLE 7

To a 12-liter three-neck reactor equipped with a mechanical stirrer, a condenser and a gas inlet, under a nitrogen atmosphere, 1,4-dioxane (5.4 liters) and dichlorodimethylsilane (600 ml) were added. The mixture was stirred in a water bath and purged with ammonia gas (400 liters). The white ammonium chloride precipitate was filtered off. The filtrate contained, in near quantitative yield, hexamethylcyclotrisilazane and octamethylcyclotetrasilazane which were identified by gas chromatograph-mass spectrometer.

EXAMPLE 8

To a 250-ml three-neck reactor equipped with mechanical stirrer, a condenser and a thermometer, under a nitrogen atmosphere, urea (2.6 g), trace ammonium bromide as catalyst, filtrate in Example 6 (50 ml) and 1,4-dioxane (50 ml) were added. The mixture was stirred and heated to reflux at about 102° C., ammonia gas was produced. After stirring for 20 minutes, the reaction mixture became viscous opaque. The mixture was continuously heated for two hours further then, cooled to 80° C. Pyridine-HBr (2.2 g) as catalyst and penicillin G sulfoxide (5.25 g, 0.015 mole) were added and stirred for 20 minutes then heated to reflux at about 102° C. After 90 minutes, additional pyridine-HBr (0.5 g) was added and the mixture was refluxed for an additional four hours. After the reaction was completed, 83% yield of product was obtained as determined by HPLC. Thereafter, the reaction mixture was cooled to room temperature and 1,4-dioxane was evaporated at reduced pressure to yield a colloidal solid residue. Water (80 ml) and dichlormethane (80 ml) were added to the residue and stirred. The pH of the aqueous phase was adjusted to 8 with N aqueous sodium hydroxide solution and active carbon (0.5 g) was added to decolorize the solution. It was then filtered and pH of the filtrate was adjusted to 1.5. The solution was filtered to yield the pale yellow solid Δ3-7-substituted amino desacetoxy cephalosporanic acid (1.91 g).

EXAMPLE 9

The procedure described in Example 8 was repeated with different types of catalysts for the ring enlargement reaction. The following results were obtained:

| No. | Ring Enlarging Agent | Amount (g) | Additional amount after 30 min. (g) | Yield (%) |
|-----|----------------------|------------|-------------------------------------|-----------|
| 1.  | Pyridine-HCl | 1.5 | 0.4 | 53 |
| 2.  | Pyridine phosphate | 2.2 | 0.6 | 59 |
| 3.  | Pyridine-1,1,1-trichloroethyl phosphate | 4 | 1 | 73 |
| 4.  | Pyridine sulfate | 2.2 | 0.6 | 41 |
| 5.  | Pyridine trichloroacetate | 3 | 0.7 | 64 |
| 6.  | Pyridine p-toluenesulfonate | 3.2 | 0.9 | 48 |
| 7.  | 2-Methylpyridine hydrobromide | 2.2 | 0.6 | 82 |
| 8.  | Aniline hydrobromide | 2.2 | 0.6 | 72 |
| 9.  | N-methylaniline hydrobromide | 2.2 | 0.7 | 72 |
| 10. | Triethylamine hydrobromide | 2.0 | 0.5 | 44 |

EXAMPLE 10

The procedure described in Example 8 was repeated with different amount of pyridine hydrobromide as catalyst. The following results were obtained.

| No. | Amount of catalyst (g) | Additional amount after 30 min. (g) | yield (%) |
|-----|------------------------|-------------------------------------|-----------|
| 1.  | 3.0 | 0.5 | 70 |
| 2.  | 2.5 | 0.5 | 78 |
| 3.  | 2.0 | 0.5 | 84 |
| 4.  | 1.5 | 0.5 | 72 |

EXAMPLE 11

The procedure described in Example 1 was repeated except that dimethylformamide as solvent was used in place of 1,1,2-trichloroethane.

EXAMPLE 12

The procedure described in Example 8 was repeated by using the reaction solution of Example 11 and DMF as diluent. The yield was 76%.

EXAMPLE 13

The procedure described in Example 2 was repeated except that penicillin V sulfoxide (5.5 g) was used in place of penicillin G sulfoxide (5.25 g). The yield was 74%.

What is claimed is:

1. A method for the preparation of $\Delta^3$-7-substituted amino desacetoxy caphalosporanic acid which comprises reacting, in the presence of an organic acid catalyst and at a temperature ranging between about 80° C. and about 150° C., (a) a penicillin sulfoxide with (b) a copolymer of urea and a mixture of hexamethylcyclotrisilazane and octamethylcyclotetrasilazane, said copolymer having a mole ratio of said urea to said mixture ranging between about 1:1 and about 2:1 and being present in an amount sufficient to esterify said penicillin sulfoxide and to remove byproduct water from the reaction, so as to form said cephalosporanic acid.

2. The method according to claim 1, wherein said reaction occurs for a period ranging between about 30 minutes and about 60 minutes.

3. The method according to claim 1, wherein said penicillin sulfoxide is penicillin G sulfoxide or penicillin V sulfoxide.

4. The method according to claim 1, wherein said organic acid catalyst comprises mineral acid or organic acid salt of pyridine, aniline or N-alkylaniline.

5. The method according to claim 4, wherein said organic acid catalyst comprises hydrobromic acid, hydrochloric acid, phosphoric acid, sulfuric acid, or trichloroacetic acid salts or pyridine, aniline or N-alkylaniline.

6. The method according to claim 5, wherein said organic acid catalyst comprises pyridine hydrobromide.

7. The method according to claim 1, wherein said copolymer comprises a product preparable by reacting said urea and said mixture of hexamethylcyclotrisilazane and octamethylcyclotetrasilazane in the presence of organic solvent and ammonium bromide catalyst and at a temperature ranging between about 50° C. and about 150° C., said ammonium bromide catalyst present in an amount ranging between about 0.1 and about 3.0 grams/liter of reaction solution.

8. A method for the preparation of $\Delta^3$-7-substituted amino desacetoxy cephalosporanic acid which comprises reacting, in the presence of an organic acid catalyst and at a temperature ranging between about 80° C. and about 150° C., (a) a dimethylsilylated ester derivative of penicillin sulfoxide with (b) a copolymer of urea and a mixture of hexamethylcyclotrisilazane and octamethylcyclotetrasilazane, said copolymer having a mole ratio of said urea to said mixture ranging between about 1:1 and about 2:1 and being present in an amount sufficient to remove by-product water from the reaction, so as to from said cephalosporanic acid.

9. The method according to claim 7, wherein said dimethylsilylated ester derivative of penicillin sulfoxide comprises a reaction product of penicillin sulfoxide with hexamethylcyclotrisilazane, octamethylcyclotetrasilazane, or 1,1,1,3,3,3-hexamethyl-disilazane.

10. The method according to claim 7, wherein said reaction occurs for a period ranging between about 30 minutes and about 60 minutes.

11. The method according to claim 7, wherein said penicillin sulfoxide is penicillin G sulfoxide or penicillin V sulfoxide.

12. The method according to claim 7, wherein said organic acid catalyst comprises mineral acid or organic acid salt of pyridine, aniline or N-alkylaniline.

13. The method according to claim 12, wherein said organic acid catalyst comprises hydrobromic acid, hydrochloric acid, phosphoric acid, sulfuric acid, or trichloroacetic acid salts of pyridine, aniline or N-alkylaniline.

14. The method according to claim 13, wherein said organic acid catalyst comprises pyridine hydrobromide.

15. The method according to claim 7, wherein said copolymer comprises a product preparable by reacting said urea and said mixture of hexamethylcyclotrisilazane and octamethylcyclotetrasilazane in the presence of organic solvent and ammonium bromide catalyst and at a temperature ranging between about 50° C. and about 150° C., said ammonium bromide catalyst present in an amount ranging between about 0.1 and about 3.0 grams/liter of reaction solution.

* * * * *